(12) United States Patent
Cadieux, Jr. et al.

(10) Patent No.: US 10,782,279 B2
(45) Date of Patent: Sep. 22, 2020

(54) METHOD FOR DETECTING OIL ON TOBACCO PRODUCTS AND PACKAGING

(71) Applicant: Altria Client Services LLC, Richmond, VA (US)

(72) Inventors: Edmond J. Cadieux, Jr., Mechanicsville, VA (US); Robert E. Wood, Nashville, TN (US)

(73) Assignee: Altria Client Services LLC, Richmond, VA (US)

( * ) Notice: Subject to any disclaimer, the term of this patent is extended or adjusted under 35 U.S.C. 154(b) by 821 days.

(21) Appl. No.: 14/938,561

(22) Filed: Nov. 11, 2015

(65) Prior Publication Data

US 2016/0131629 A1 May 12, 2016

Related U.S. Application Data

(60) Provisional application No. 62/078,290, filed on Nov. 11, 2014.

(51) Int. Cl.
| | | |
|---|---|---|
| *G01N 33/28* | (2006.01) | |
| *G01N 21/64* | (2006.01) | |
| *G01N 21/94* | (2006.01) | |
| *G01N 33/00* | (2006.01) | |

(52) U.S. Cl.
CPC ......... *G01N 33/28* (2013.01); *G01N 21/643* (2013.01); *G01N 21/6447* (2013.01); *G01N 21/94* (2013.01); *G01N 2021/6441* (2013.01)

(58) Field of Classification Search
CPC ........ G01N 33/28; G01N 33/26; G01N 33/00; G01N 21/643; G01N 21/6428; G01N 21/64; G01N 21/63; G01N 21/62

USPC .......................................................... 436/60
See application file for complete search history.

(56) References Cited

U.S. PATENT DOCUMENTS

| | | |
|---|---|---|
| 3,085,581 A | 4/1963 | Rosenberg |
| 3,111,950 A | 11/1963 | Martinus Verbakel |
| 3,417,241 A | 12/1968 | Davis |
| 3,806,727 A | 4/1974 | Leonard et al. |
| 3,812,349 A | 5/1974 | Gugliotta et al. |
| 3,880,289 A | 4/1975 | Gray |
| 3,985,581 A | 10/1976 | Stachurski |
| RE29,298 E | 7/1977 | Banks |

(Continued)

FOREIGN PATENT DOCUMENTS

| | | |
|---|---|---|
| CA | 2837315 | 11/2012 |
| DE | 20320957 U1 | 7/2005 |

(Continued)

OTHER PUBLICATIONS

International Search Report of International Application No. PCT/US2014/026556 dated Aug. 5, 2014.

(Continued)

*Primary Examiner* — Christine T Mui
(74) *Attorney, Agent, or Firm* — Harness, Dickey & Pierce, P.L.C.

(57) ABSTRACT

A process for detecting oil or lubricant contamination in a manufactured product, the process comprising adding at least two fluorescent taggants to oils or lubricants contained in processing machinery for said product, irradiating said product, causing at least one of said taggants to fluoresce and detecting radiation emitted by said fluorescing taggant in an oil-contaminated product.

36 Claims, 1 Drawing Sheet

(56) References Cited

U.S. PATENT DOCUMENTS

| | | |
|---|---|---|
| 4,057,721 A | 11/1977 | deVial et al. |
| 4,175,996 A | 11/1979 | Battard et al. |
| 4,445,520 A | 5/1984 | Knight et al. |
| 4,480,702 A | 11/1984 | Kelly, Jr. |
| 4,657,144 A | 4/1987 | Peter et al. |
| 4,845,374 A | 7/1989 | White et al. |
| 4,858,465 A | 8/1989 | Molina |
| 4,971,077 A | 11/1990 | Dominguez et al. |
| 5,048,543 A | 9/1991 | Smith |
| 5,092,349 A | 3/1992 | Smith et al. |
| 5,134,291 A | 7/1992 | Ruhl, Jr. et al. |
| 5,265,732 A | 11/1993 | Long |
| 5,414,270 A | 5/1995 | Henderson et al. |
| 5,440,919 A | 8/1995 | Cooper |
| 5,462,176 A | 10/1995 | Hereford et al. |
| 5,476,108 A | 12/1995 | Dominguez et al. |
| 5,525,516 A | 6/1996 | Krutak et al. |
| 5,554,480 A | 9/1996 | Patel et al. |
| 5,665,538 A | 9/1997 | Howard et al. |
| 5,710,046 A | 1/1998 | Rutledge et al. |
| 5,715,843 A | 2/1998 | Hapke et al. |
| 5,764,874 A | 6/1998 | White |
| 5,804,447 A | 9/1998 | Albert et al. |
| 5,807,605 A | 9/1998 | Tingey et al. |
| 5,846,830 A | 12/1998 | Demello et al. |
| 5,887,073 A | 3/1999 | Fazzari et al. |
| 5,974,860 A | 11/1999 | Kuroda et al. |
| 5,990,197 A | 11/1999 | Escano et al. |
| 5,998,211 A | 12/1999 | Albert et al. |
| 6,025,200 A | 2/2000 | Kaish et al. |
| 6,058,940 A | 5/2000 | Lane |
| 6,060,677 A | 5/2000 | Ulrichsen et al. |
| 6,064,032 A | 5/2000 | Voss et al. |
| 6,123,201 A | 9/2000 | Atwell et al. |
| 6,135,386 A | 10/2000 | Garthaffner |
| 6,149,719 A | 11/2000 | Houle |
| 6,166,366 A | 12/2000 | Lewis et al. |
| 6,312,958 B1 | 11/2001 | Meyer et al. |
| 6,380,547 B1 | 4/2002 | Gonzalez et al. |
| 6,384,359 B1 | 5/2002 | Belcastro et al. |
| 6,444,143 B2 | 9/2002 | Bawendi et al. |
| 6,477,227 B1 | 11/2002 | Kaiser et al. |
| 6,511,756 B1 | 1/2003 | Obuchi et al. |
| 6,529,273 B1 | 3/2003 | Norris et al. |
| 6,633,043 B2 | 10/2003 | Hegazi et al. |
| 6,734,383 B1 | 5/2004 | Calcoen et al. |
| 6,771,365 B1 | 8/2004 | Pirani |
| 6,795,179 B2 | 9/2004 | Kumar |
| 6,809,819 B1 | 10/2004 | Vinjamoori |
| 6,830,310 B2 | 12/2004 | Iu et al. |
| 6,905,538 B2 | 6/2005 | Auslander |
| 6,914,678 B1 | 7/2005 | Ulrichsen et al. |
| 6,926,764 B2 | 8/2005 | Bleikolm et al. |
| 7,124,944 B2 | 10/2006 | Selinfreund et al. |
| 7,142,296 B2 | 11/2006 | Cunningham et al. |
| 7,153,557 B2 | 12/2006 | Rancien |
| 7,157,611 B2 | 1/2007 | Banavali et al. |
| 7,227,148 B2 | 6/2007 | Sato et al. |
| 7,256,398 B2 | 8/2007 | Ross et al. |
| 7,319,039 B2 | 1/2008 | Sullivan |
| 7,378,675 B2 | 5/2008 | Ross et al. |
| 7,391,035 B2 | 6/2008 | Kong et al. |
| 7,441,704 B2 | 10/2008 | Ross |
| 7,488,945 B2 | 2/2009 | Li et al. |
| 7,538,324 B2 | 5/2009 | Deevi et al. |
| 7,705,144 B2 | 4/2010 | Holmes |
| 7,749,438 B2 | 7/2010 | Zeinali et al. |
| 7,767,457 B2 | 8/2010 | Mun et al. |
| 7,768,643 B1 | 8/2010 | Janssens et al. |
| 7,787,111 B2 | 8/2010 | Kim et al. |
| 7,800,088 B2 | 9/2010 | Ross et al. |
| 7,812,953 B2 | 10/2010 | Tai et al. |
| 7,816,616 B2 | 10/2010 | Kenny |
| 7,829,162 B2 | 11/2010 | Eskra et al. |
| 7,842,896 B1 | 11/2010 | Calcoen et al. |
| 7,919,325 B2 | 4/2011 | Eastwood et al. |
| 7,938,124 B2 | 5/2011 | Izumiya et al. |
| 7,985,590 B2 | 7/2011 | McNeil |
| 8,415,165 B2 | 4/2013 | Liang et al. |
| 8,641,933 B2 | 2/2014 | Purdy et al. |
| 8,692,148 B1 | 4/2014 | Sommer |
| 9,006,599 B2 | 4/2015 | Adams |
| 9,073,091 B2 | 7/2015 | Cadieux, Jr. |
| 9,080,987 B2 | 7/2015 | Faenza |
| 9,097,668 B2 | 8/2015 | Cadieux, Jr. |
| 9,174,245 B2 | 11/2015 | Blanc et al. |
| 9,244,017 B2 | 1/2016 | Cadieux, Jr. et al. |
| 9,361,561 B2 | 6/2016 | Bown et al. |
| 9,546,966 B2 | 1/2017 | Cadieux, Jr. et al. |
| 9,733,197 B2 | 8/2017 | Cadieux, Jr. et al. |
| 9,791,407 B2 | 10/2017 | Urey et al. |
| 2001/0045378 A1* | 11/2001 | Charles ............. B07C 5/3412 209/3.3 |
| 2002/0074269 A1 | 6/2002 | Hensley et al. |
| 2002/0094058 A1 | 7/2002 | Kaiser et al. |
| 2002/0097833 A1 | 7/2002 | Kaiser et al. |
| 2002/0122878 A1 | 9/2002 | Kerns et al. |
| 2002/0158212 A1 | 10/2002 | French et al. |
| 2003/0034282 A1 | 2/2003 | Safai |
| 2003/0036201 A1 | 2/2003 | Nelson et al. |
| 2003/0058990 A1 | 3/2003 | Kaiser et al. |
| 2003/0097833 A1 | 5/2003 | Ingram et al. |
| 2003/0129283 A1 | 7/2003 | Martinez Carballido |
| 2003/0141459 A1 | 7/2003 | Hegazi et al. |
| 2003/0183326 A1 | 10/2003 | O'Connor |
| 2003/0194052 A1 | 10/2003 | Price et al. |
| 2004/0134504 A1 | 7/2004 | Lane |
| 2005/0029469 A1 | 2/2005 | Schroder et al. |
| 2005/0031838 A1 | 2/2005 | Lagunowich et al. |
| 2005/0083720 A1 | 4/2005 | Fukui et al. |
| 2005/0092336 A1 | 5/2005 | Zielke et al. |
| 2005/0092408 A1 | 5/2005 | Lauf et al. |
| 2005/0099475 A1 | 5/2005 | Barreto |
| 2005/0236015 A1 | 10/2005 | Goel et al. |
| 2005/0241989 A1 | 11/2005 | Sant et al. |
| 2005/0276906 A1 | 12/2005 | Metzger |
| 2006/0016735 A1 | 1/2006 | Ito et al. |
| 2006/0081503 A1 | 4/2006 | Wegner |
| 2006/0118741 A1 | 6/2006 | Ross et al. |
| 2006/0131517 A1 | 6/2006 | Ross et al. |
| 2006/0131518 A1 | 6/2006 | Ross et al. |
| 2006/0186348 A1 | 8/2006 | Nguyen et al. |
| 2006/0241499 A1 | 10/2006 | Irion et al. |
| 2006/0246020 A1 | 11/2006 | Cole et al. |
| 2006/0262318 A1 | 11/2006 | Sullivan |
| 2006/0291872 A1 | 12/2006 | Mei et al. |
| 2007/0023715 A1 | 2/2007 | Ross et al. |
| 2007/0048761 A1 | 3/2007 | Reep et al. |
| 2007/0084269 A1 | 4/2007 | Quest et al. |
| 2007/0187617 A1 | 8/2007 | Kong et al. |
| 2007/0239367 A1 | 10/2007 | Odegard et al. |
| 2008/0030712 A1 | 2/2008 | Tokhtuev et al. |
| 2008/0116272 A1 | 5/2008 | Giering et al. |
| 2008/0121815 A1 | 5/2008 | Agrawal et al. |
| 2009/0032733 A1 | 2/2009 | Thabeth et al. |
| 2009/0047531 A1 | 2/2009 | Bartley et al. |
| 2009/0097833 A1 | 4/2009 | Imada |
| 2009/0104711 A1 | 4/2009 | Sim |
| 2009/0185182 A1 | 7/2009 | Kim et al. |
| 2009/0237645 A1 | 9/2009 | Hamby et al. |
| 2009/0280341 A1 | 11/2009 | Maruichi et al. |
| 2009/0321623 A1 | 12/2009 | Ross et al. |
| 2010/0080456 A1 | 4/2010 | Paul et al. |
| 2010/0163063 A1 | 7/2010 | Fernando et al. |
| 2010/0219377 A1 | 9/2010 | Ebert |
| 2010/0224795 A1 | 9/2010 | Cole et al. |
| 2010/0226861 A1 | 9/2010 | Cole et al. |
| 2010/0233447 A1 | 9/2010 | Campbell |
| 2010/0290040 A1 | 11/2010 | Berghmans |
| 2010/0320371 A1 | 12/2010 | Agrawal et al. |
| 2011/0141272 A1 | 6/2011 | Uto et al. |
| 2011/0151576 A1 | 6/2011 | Perfect et al. |
| 2011/0168915 A1 | 7/2011 | Yajima et al. |
| 2011/0216190 A1 | 9/2011 | Shimazu et al. |

(56) References Cited

U.S. PATENT DOCUMENTS

| | | | |
|---|---|---|---|
| 2012/0104278 | A1 | 5/2012 | Downing et al. |
| 2012/0267287 | A1 | 10/2012 | Bailey |
| 2012/0302474 | A1 | 11/2012 | Faenza |
| 2013/0082173 | A1 | 4/2013 | Cadieux et al. |
| 2013/0179090 | A1 | 7/2013 | Conroy et al. |
| 2013/0188170 | A1 | 7/2013 | Wilkins |
| 2013/0320216 | A1 | 12/2013 | Aiko |
| 2013/0320237 | A1 | 12/2013 | Cadieux et al. |
| 2014/0262966 | A1 | 9/2014 | Cadieux, Jr. |
| 2015/0008162 | A1 | 1/2015 | Cadieux, Jr. |
| 2015/0048250 | A1 | 2/2015 | Cadieux, Jr. et al. |
| 2015/0290684 | A1 | 10/2015 | Cadieux, Jr. |
| 2015/0315511 | A1 | 11/2015 | Faenza |
| 2015/0323459 | A1 | 11/2015 | Cadieux, Jr. |
| 2016/0108293 | A1 | 4/2016 | Cadieux, Jr. et al. |
| 2016/0131596 | A1 | 5/2016 | Cadieux, Jr. et al. |
| 2016/0131629 | A1 | 5/2016 | Cadieux, Jr. et al. |

FOREIGN PATENT DOCUMENTS

| | | |
|---|---|---|
| DE | 102011007666 A1 | 10/2012 |
| EP | 0146299 A1 | 6/1985 |
| EP | 0223446 A2 | 5/1987 |
| EP | 657028 A1 | 6/1995 |
| EP | 0897762 A2 | 2/1999 |
| EP | 2715320 A2 | 4/2014 |
| GB | 2091416 | 7/1982 |
| JP | S61290057 A | 6/1985 |
| JP | S64059095 A | 3/1989 |
| JP | H04473 | 1/1992 |
| JP | H06066728 A | 3/1994 |
| JP | H09-309845 | 12/1997 |
| JP | 2000-273757 | 10/2000 |
| JP | 2002505426 A | 2/2002 |
| JP | 2002513155 A | 5/2002 |
| JP | 2004-524013 A | 8/2004 |
| JP | 2005-037398 | 2/2005 |
| JP | 3907042 | 1/2007 |
| JP | 2009519459 A | 5/2009 |
| JP | 2009-229466 | 10/2009 |
| JP | 2011-158425 A | 8/2011 |
| JP | 2014512185 A | 5/2014 |
| JP | 2014515487 A | 6/2014 |
| WO | 1991017265 A1 | 11/1991 |
| WO | WO-92/07249 A1 | 4/1992 |
| WO | 9800243 A1 | 1/1998 |
| WO | 9957417 | 11/1999 |
| WO | 1999057417 A2 | 11/1999 |
| WO | 2001025747 A2 | 4/2001 |
| WO | 2001025748 A2 | 4/2001 |
| WO | 2001025764 A1 | 4/2001 |
| WO | 2001025766 A1 | 4/2001 |
| WO | 2001025767 A1 | 4/2001 |
| WO | 2001025820 A2 | 4/2001 |
| WO | 2002068945 A1 | 9/2002 |
| WO | WO-2006058406 A1 | 6/2006 |
| WO | 2008049515 A2 | 5/2008 |
| WO | 2010007390 A1 | 1/2010 |
| WO | WO-2010/018216 A2 | 2/2010 |
| WO | 2012030988 A1 | 3/2012 |
| WO | 2012050844 A1 | 4/2012 |
| WO | 2012162701 A1 | 11/2012 |
| WO | 2013181286 A1 | 12/2013 |
| WO | 2014168720 A2 | 10/2014 |

OTHER PUBLICATIONS

International Search Report of International Application No. PCT/US2012/039870 dated Aug. May 26, 2011.
International Search Report of International Application No. PCT/US2013/043172 dated Aug. 6, 2013.
Victoria B. Rodriguez et al., "Encapsulation and stabilization of indocyanine green within poly (styrene-alt-maleic anhydride) block-poly (styrene) micelles for near-infrared imaging" Journal of Biomedical Optics, SPIE—International Society for Optical Engineering,vol. 13 No. 1, Jan. 30, 2008, p. 14025-1-140025-10; XP002664215.
International Preliminary Report on Patentability of International Application No. PCT/US2014/026556 dated Sep. 15, 2015.
International Preliminary Report on Patentability of International Application No. PCT/US2013/043172 dated Dec. 2, 2014.
International Preliminary Report on Patentability of International Application No. PCT/US2012/039870 dated Nov. 26, 2013.
International Search Report & Written Opinion issued in International Patent Application Na PCT/US2015/060179, dated Feb. 8, 2016.
Office Action for corresponding U.S. Appl. No. 14/883,200 dated Oct. 16, 2018.
Office Action for corresponding Mexican Application No. MX/a/2013/013768 dated May 23, 2018 and English translation thereof.
Non-Final Office Action dated Nov. 7, 2017 in U.S. Appl. No. 15/653,377.
Notice of Allowance dated May 23, 2018 in U.S. Appl. No. 15/653,377.
Non-Final Office Action dated Oct. 19, 2016 in U.S. Appl. No. 14/994,972.
Notice of Allowance dated Apr. 5, 2017 in U.S. Appl. No. 14/994,972.
Non-Final Office Action dated Jan. 29, 2015 in U.S. Appl. No. 13/482,771.
Final Office Action dated Jun. 8, 2015 in U.S. Appl. No. 13/482,771.
Notice of Allowance dated Sep. 14, 2015 in U.S. Appl. No. 13/482,771.
Non-Final Office Action dated May 21, 2014 in U.S. Appl. No. 13/338,971.
Final Office Action dated Sep. 10, 2014 in U.S. Appl. No. 13/338,971.
Notice of Allowance dated Jan. 2, 2015 in U.S. Appl. No. 13/338,971.
Decision of Rejection for Japanese Application No. 2017-073848 dated Sep. 7, 2018.
Office Action dated Feb. 15, 2018 in Japanese Patent Application No. 2017-073848.
Office Action dated Mar. 29, 2016 in Japanese Patent Application No. 2014-512185.
Office Action dated Dec. 2, 2016 in Japanese Patent Application No. 2014-512185.
Notice of Allowance dated Aug. 29, 2018 in Japanese Patent Application No. 2014-512185.
Notice of Allowance dated May 16, 2018 in Canadian Patent Application No. 2,837,315.
Office Action dated Sep. 20, 2018 for corresponding U.S. Appl. No. 14/795,674.
Non-Final Office Action for corresponding U.S. Appl. No. 13/904,968 dated Feb. 1, 2019.
Notice of Allowance for U.S. Appl. No. 14/795,674, dated May 15, 2019.
United States Office Action for U.S. Appl. No. 14/883,200, dated Apr. 29, 2019.
United States Office Action for corresponding U.S. Appl. No. 16/253,674 dated Mar. 15, 2019.
United States Office Action for corresponding U.S. Appl. No. 14/938,561 dated Mar. 20, 2019.
European European Office Action for corresponding Application No. 12727705.1-1020 dated Mar. 7, 2019.
United States Office Action for U.S. Appl. No. 13/904,968, dated Aug. 8, 2019.
United States Office Action for U.S. Appl. No. 16/253,674, dated Sep. 3, 2019.
Japanese Office Action for corresponding Application No. 2017-525056, dated Aug. 27, 2019, English translation thereof.
European Office Action for corresponding Application No. 15813150-8-1230, dated Oct. 9, 2019.
United States Office Action for U.S. Appl. No. 16/127,711, dated Nov. 1, 2019.
Japanese Office Action for corresponding Application No. 2018-246546, dated Nov. 1, 2019, English translation thereof.
United States Office Action for U.S. Appl. No. 14/883,200, dated Dec. 26, 2019.

(56) References Cited

OTHER PUBLICATIONS

Canadian Office Action for corresponding Application No. 3,023,128, dated Dec. 16, 2019.
United States Notice of Allowance for U.S. Appl. No. 14/938,561, dated Feb. 11, 2020.
Japanese Office Action for corresponding Application No. 2017-525056, dated Mar. 3, 2020, English translation thereof.
United States Office Action for U.S. Appl. No. 13/904,968, dated Feb. 4, 2020.
United States Notice of Allowance for U.S. Appl. No. 16/127,711, dated Mar. 25, 2020.
United States Office Action for U.S. Appl. No. 14/883,200, dated May 8, 2020.
United States Notice of Allowance for U.S. Appl. No. 14/795,674, dated Jun. 2, 2020.
United States Office Action for U.S. Appl. No. 13/904,968, dated Aug. 6, 2020.

* cited by examiner

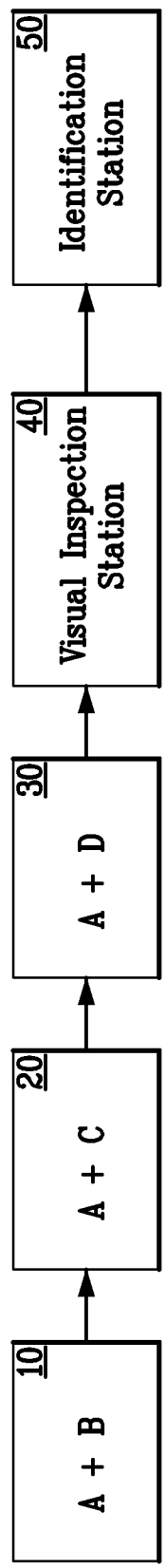

METHOD FOR DETECTING OIL ON TOBACCO PRODUCTS AND PACKAGING

RELATED APPLICATION

This application claims priority to U.S. Provisional Application No. 62/078,290, filed Nov. 11, 2014, the contents of which are hereby incorporated by reference in their entirety.

FIELD

Disclosed herein is an inspection process for detection of oil and/or grease (lubricants) contamination on tobacco, tobacco products, food, pharmaceuticals, packaging, and other consumer goods and products.

ENVIRONMENT

In the processing and packaging of consumer products and products designed to provide tobacco enjoyment, oils, greases and other such lubricants may inadvertently come into contact with the product being produced.

In the case of products designed to provide tobacco enjoyment, tobacco leaf is processed prior to the time that it is provided as final product. For example, leaf may be contacted by machinery during harvesting, curing and transport to a stemmery. When leaf is provided in strip form at a stemmery, and cut or otherwise shredded to the desired size, it is possible for oils, greases and lubricants to inadvertently come into contact with the tobacco. Likewise, lubricants used in operating the various machines used in the processing of the tobacco can inadvertently come into contact with that tobacco. The sources of lubricant contamination can vary, such as when a particular piece of machinery or component of that piece of machinery fails to operate in an optimum fashion. Additionally, lubricants may inadvertently come into contact with tobacco due to leakage of lubricants through gaskets or seals, from sliding mechanisms, from drum systems, from gear boxes, from pumps, from sealed rolling bearing units, from chains and belts, and the like. Lubricants are used in conditioning cylinders, threshers, separators, redryers, receivers, feeders, conveyors, cutters, blenders, tobacco presses and other such pieces of equipment that are commonly used in tobacco stemmeries, and in tobacco primary processing operations.

Lubricants of similar compositions are used throughout the various stages of tobacco treatment and cigarette manufacture. Heretofore, it has been difficult for the cigarette manufacturer to detect the presence of oil in its tobacco and/or its cigarettes and to locate the source of a particular lubricant once it has been detected. For example, conventional detection is by visual observation of a spot on a wrapped tobacco rod, followed by removal of the contaminated object and laboratory analysis, which is a time consuming process.

It would be advantageous if the inspection of machine-processed products, such as tobacco and tobacco products, for the presence of a lubricant or the like could be facilitated.

SUMMARY

In one aspect, disclosed is a process for detecting oil or lubricant contamination in a manufactured product, the process comprising adding at least two fluorescent taggants to oils or lubricants contained in processing machinery for said product, irradiating said product, causing at least one of said taggants to fluoresce, and detecting radiation emitted by said fluorescing taggant in an oil-contaminated product.

In one form, at least one of said fluorescent taggants fluoresces upon irradiation with ultraviolet radiation.

In one form, the at least one fluorescent taggant emits radiation in the visible spectrum.

In one form, both of said fluorescent taggants fluoresce upon irradiation with ultraviolet radiation.

In one form, the fluorescent taggants are added to said oils or lubricants at different concentration levels, with at least one taggant being added at a sufficient concentration level for its emission to be visually detectable by an operator of said process.

In one form, at least one fluorescent taggant is added to said oils or lubricants at a concentration of between about 50 ppb and about 100 ppm.

In one form, the process further comprises conveying said product past an electronic radiation detection apparatus which detects radiation emitted by said fluorescing taggant.

In one form, the fluorescent taggants are Stokes-shifting taggants, which absorb radiation at a first wavelength and fluoresce at a second wavelength, different from said first wavelength.

In one form, the product is a cigarette rod which is wrapped in paper.

In one form, the product is a food product.

In one form, one or both of the fluorescent taggants is oil soluble.

In one form, one or both of the fluorescent taggants is oil dispersible.

In another aspect, disclosed is a process for detecting oil or lubricant contamination in a tobacco product, the process comprising adding at least two fluorescent taggants to oils or lubricants contained in processing machinery for said product, irradiating said product, causing at least one of said taggants to fluoresce, and detecting radiation emitted by said fluorescing taggant in an oil-contaminated product.

In one form, at least one of said fluorescent taggants fluoresces upon irradiation with ultraviolet radiation.

In one form, the at least one fluorescent taggant emits radiation in the visible spectrum.

In one form, both of said fluorescent taggants fluoresce upon irradiation with ultraviolet radiation.

In one form, the fluorescent taggants are added to said oils or lubricants at different concentration levels, with at least one taggant being added at a sufficient concentration level for its emission to be visually detectable by an operator of said process.

In one form, at least one fluorescent taggant is added to said oils or lubricants at a concentration of between about 50 ppb and about 100 ppm.

In one form, the process further comprises conveying said product past an electronic radiation detection apparatus which detects radiation emitted by said fluorescing taggant.

In one form, the fluorescent taggants are Stokes-shifting taggants, which absorb radiation at a first wavelength and fluoresce at a second wavelength, different from said first wavelength.

In one form, the product is a cigarette rod which is wrapped in paper.

In one form, the product is a food product.

In one form, one or both of the fluorescent taggants is oil soluble.

In one form, one or both of the fluorescent taggants is oil dispersible.

In yet another aspect, disclosed is a process for identifying the source of oil contamination of products produced in a manufacturing process having multiple machines in series, each containing one or more oils or lubricants, comprising adding a first fluorescent taggant to all of the oils or lubricants of each machine in the series, adding a second fluorescent taggant to each oil or lubricant of each machine in the series, different from said first fluorescent taggant and unique to each oil or lubricant of each machine in the series, irradiating the product with a first radiation spectrum and detecting radiation emitted by the first fluorescent taggant and removing the radiation emitting product from the process.

In one form, the process further comprises irradiating the removed product with a second radiation spectrum and detecting radiation emitted by said second fluorescent taggant, so as to identify the source of said contamination.

In one form, detection of radiation emitted by said second fluorescent taggant is conducted with an electronic radiation detection apparatus.

In one form, detection of radiation emitted by the first fluorescent taggant is conducted visually by an operator of said process.

In one form, the first fluorescent taggant is added to said oils or lubricants at a sufficient concentration level for its emission to be visually detectable by an operator of said process.

In one form, said fluorescent taggants are Stokes-shifting taggants, which absorb radiation at a first wavelength and fluoresce at a second wavelength, different from said first wavelength.

In one form, at least said first fluorescent taggant absorbs radiation in the ultraviolet spectrum and emits radiation in the visible spectrum.

In one form, the machines include one for preparing a raw material for shipping.

In one form, the machines include a packaging machine.

In one form, detection of radiation emitted by said first fluorescent taggant is conducted with an electronic radiation detection apparatus mounted on or within at least one of said multiple machines in said series.

In one form, detection of radiation emitted by said first fluorescent taggant is conducted visually by an operator of the process, and detection of radiation emitted by said second fluorescent taggant is conducted with an electronic radiation detection apparatus.

In one form, detection of radiation emitted by said first fluorescent taggant is conducted with an electronic radiation detection apparatus mounted on or within at least one of said multiple machines in said series, and detection of radiation emitted by said second fluorescent taggant is conducted with an electronic radiation detection apparatus located separately from said first electronic radiation detection apparatus.

BRIEF DESCRIPTION OF THE DRAWINGS

The forms disclosed herein are illustrated by way of example, and not by way of limitation, in the FIGURES of the accompanying drawings and in which like reference numerals refer to similar elements and in which:

The FIGURE presents a diagrammatic illustration of one sequence of the process of the invention.

DETAILED DESCRIPTION

Various aspects will now be described with reference to specific forms selected for purposes of illustration. It will be appreciated that the spirit and scope of the apparatus, system and methods disclosed herein are not limited to the selected forms.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Disclosed herein is a method of detecting oil and/or grease found on tobacco products and/or packaging through the use of taggants. In this method a taggant is added to oil/grease, such as that in a piece of manufacturing equipment or involved in a manufacturing process, that may come into contact with the tobacco product and/or packaging. If the taggant is then detected, the product is removed as it is contaminated. Additionally, a second taggant can be added to oil as a "discriminating taggant", which is unique for a particular machine or area of the process. Once oil is detected using the primary taggant, the oil spot can be further interrogated by an offline instrument to determine the source of the "discriminating taggant" and further aid personnel in pinpointing the course of the manufacturing challenge.

In one form, the detection system disclosed herein can be used in many processes and for consumer products which are susceptible to lubricant contamination during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, lumber or any other manufactured or packaged product wherein an absence of oil is desired.

In one embodiment, the process comprises adding at least two fluorescent taggants to oils or lubricants contained in processing machinery for said product, such as a tobacco product, irradiating said product, causing at least one of said taggants to fluoresce, and detecting radiation emitted by said fluorescing taggant in an oil-contaminated product. Advantageously, at least one of said fluorescent taggants fluoresces upon irradiation with ultraviolet radiation, and emits radiation in the visible spectrum, so as to be easily detected by an observer.

In a more preferred embodiment, both of said fluorescent taggants fluoresce upon irradiation with ultraviolet radiation, at least the first of which emits radiation in the visible spectrum. Preferably, the fluorescent taggants are Stokes-shifting taggants, which absorb radiation at a first wavelength and fluoresce at a second wavelength, different from said first wavelength.

According to the process of the present invention, the product can be conveyed past an electronic radiation detection apparatus which detects radiation emitted by said fluorescing taggant(s). The product can be a tobacco product, such as a cigarette rod wrapped in paper, or a food product.

Suitable fluorescent taggants include those which are oil soluble and those which are oil dispersible. Preferred taggant compounds fluoresce at specific wavelengths from about 390 nm to about 700 nm. More preferred taggant compounds fluoresce at specific wavelengths from about 425 nm to about 625 nm. For example, after irradiation with UV light, a taggant compound may fluoresce at a wavelength of 465 nm, 510 nm or 530 nm. In another embodiment, the taggant compound is a UV sensitive compound (emits visible light in response to UV radiation). In many instances, since the machine-processed product may be subject to handling or ingestion by consumers, it is advantageous to utilize organic taggants, especially those which demonstrate little or no toxicity.

Examples of organic taggant compounds include pyrazolines, oxinates, benzoxazinones, benzimidazoles, benzthiazoles, thioxanthenes, anthranilic acids, terephthalic acids, aldazines, coumarines, barbituric acids, lumiphores, oxazoles, thiazoles, cumene, stilbenes, and derivatives thereof, such as phytochrome, riboflavin, aryl-acetylenes, 2,5-diaryl-oxazoles, 1,2,3-oxadiazoles, aryl-substituted 2-pyrazolidines, xanthones, thioxanthones and acridones, benzazoles, benzotriazoles, benzoquinolines, fluoresceine derivatives, derivatives of phenothiazine, phenoxazine, quinine derivatives (including quinine derivatives having fused aromatic rings), coumarins, indigo derivatives, derivatives of naphthalic anhydride and naphthalimide, perilenes and the like.

The fluorescent taggants can be added to said oils or lubricants at different concentration levels, with at least one taggant being added at a sufficient concentration level for its emission to be visually detectable by an operator of said process. Accordingly, at least one fluorescent taggant is added to said oils or lubricants at a concentration of between about 50 ppb and 100 about ppm, or between about 10 ppm and 100 about ppm.

However, in order to provide for easier treatment of oils or lubricants already in place within various machines, it can be more convenient to formulate a master batch of at least the first taggant in any particular oil, wherein the taggant is mixed at higher concentrations in the base oil/lubricant, such as from about 0.1 to about 5 wt % taggant, or even from about 0.2 to about 2 wt % taggant, in a balance of the base oil/lubricant. A portion of such tagged master batch is then easily transported and added to oils/lubricants which are already in place in the machines to be treated, for example by adding a small amount of the tagged master batch to the oil sump of the machine. The second, discriminating taggants can be added either directly to the particular machine oil to be treated, or added to different portions of the tagged master batch, and then added to the appropriate machine.

When the taggant is not an oil-soluble taggant, an optional surfactant or dispersant additive can be added in an amount effective to facilitate dispersion of the taggant particles in the base oil. Such surfactants/dispersants are well-known in the art and their identities need not be repeated herein.

According to the present invention, a detectable taggant compound is added to the various lubricants used in manufacturing and processing machinery, and advantageously taggant compounds having different characteristics are added into the lubricants at different processing locations, such that detection of one or more of these taggant compounds can enable rapid identification of the location of the source of lubricant contamination in the manufactured product.

Thus, in another embodiment the invention is directed to a process for identifying the source of oil contamination of products produced in a manufacturing process having multiple machines in series, each containing one or more oils or lubricants, comprising adding a first fluorescent taggant to all of the oils or lubricants of each machine in the series, adding a second fluorescent taggant to each oil or lubricant of each machine in the series, different from said first fluorescent taggant and unique to each oil or lubricant of each machine in the series, irradiating the product with a first radiation spectrum and detecting radiation emitted by the first fluorescent taggant and removing the radiation emitting product from the process.

The process further comprises irradiating the removed product with a second radiation spectrum and detecting radiation emitted by said second fluorescent taggant, so as to identify the source of said contamination.

In one embodiment, detection of radiation emitted by said first fluorescent taggant is conducted visually by an operator of said process, and optionally detection of the second fluorescent taggant is conducted with an electronic radiation detection apparatus. Accordingly, the first fluorescent taggant is added to said oils or lubricants at a sufficient concentration level for its emission to be visually detectable by an operator of said process. Similarly to the above disclosure, the fluorescent taggants are Stokes-shifting taggants, which absorb radiation at a first wavelength and fluoresce at a second wavelength, different from said first wavelength, especially wherein at least the first fluorescent taggant absorbs radiation in the ultraviolet spectrum and emits radiation in the visible spectrum.

Conversely, in another embodiment detection of radiation emitted by said first fluorescent taggant is conducted with an electronic radiation detection apparatus mounted on or within at least one of multiple machines in said series.

Additionally, detection of radiation emitted by said first fluorescent taggant can be conducted visually by an operator of the process, and detection of radiation emitted by said second fluorescent taggant can be conducted with an electronic radiation detection apparatus.

Likewise, in another alternative the process can be conducted such that detection of radiation emitted by said first fluorescent taggant is conducted with an electronic radiation detection apparatus mounted on or within at least one of said multiple machines in said series, and detection of radiation emitted by said second fluorescent taggant can be conducted with an electronic radiation detection apparatus located separately from said first electronic radiation detection apparatus.

In the accompanying FIGURE, three processing machines, 10, 20 and 30 have a first fluorescent compound A added to the oil or lubricant of each machine. This first fluorescent compound A can be irradiated with such as ultraviolet radiation and fluoresces in the visible spectrum, such that its presence can be visually identified in a visual inspection station 40. Upon observation of contamination of the first fluorescent compound, the contaminated product is removed and sent to identification station 50. Each of machines 10, 20 and 30 also have differing second fluorescent compounds B, C and D added to the oil or lubricant of each machine. Each second fluorescent compound can be irradiated with such as ultraviolet radiation at the identification station 50, and each will produce an emission at differing wavelengths, which allows the inspector to identify from which machine 10, 20 or 30 the contamination has originated. Because under the teachings herein, an inexpensive ultraviolet light fixture or a hand-held ultraviolet light unit may be used as a source and because the common taggant "A" responds in the visible light spectrum (avoiding the need for expensive detectors), the teachings herein provide an inexpensive, yet effective way to check for the presence of oil on an on-line basis, with little or no impact on operations or safety.

The machines suitable for treating with the presently disclosed system and process include those for preparing a raw material for shipping, such as a packaging machine.

The embodiments disclosed herein, as illustratively described and exemplified hereinabove, have several beneficial and advantageous aspects, characteristics, and features. The embodiments disclosed herein successfully address and overcome shortcomings and limitations, and widen the scope, of currently known teachings with respect to the detection of oil and lubricants on tobacco products or packaging.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and define a term in a manner or are otherwise inconsistent with either the non-incorporated portion of the present disclosure or with any of the other incorporated references, the non-incorporated portion of the present disclosure shall control, and the term or incorporated disclosure therein shall only control with respect to the reference in which the term is defined and/or the incorporated disclosure was originally present.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Illustrative, non-exclusive examples of apparatus and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT1. A process for detecting oil or lubricant contamination in a manufactured product, the process comprising: adding at least two fluorescent taggants to oils or lubricants contained in processing machinery for said product; irradiating said product, causing at least one of said taggants to fluoresce; and detecting radiation emitted by said fluorescing taggant in an oil-contaminated product.

PCT2. The process of paragraph PCT1, wherein at least one of said fluorescent taggants fluoresces upon irradiation with ultraviolet radiation.

PCT3. The process of paragraph PCT2, wherein said at least one fluorescent taggant emits radiation in the visible spectrum.

PCT4. The process of any preceding paragraph, wherein both of said fluorescent taggants fluoresce upon irradiation with ultraviolet radiation.

PCT5. The process of any preceding paragraph, wherein the fluorescent taggants are added to said oils or lubricants at different concentration levels, with at least one taggant being added at a sufficient concentration level for its emission to be visually detectable by an operator of said process.

PCT6. The process of any preceding paragraph, wherein at least one fluorescent taggant is added to said oils or lubricants at a concentration of between about 50 ppb and about 100 ppm.

PCT7. The process of any preceding paragraph, further comprising conveying said product past an electronic radiation detection apparatus which detects radiation emitted by said fluorescing taggant.

PCT8. The process of any preceding paragraph, wherein said fluorescent taggants are Stokes-shifting taggants, which absorb radiation at a first wavelength and fluoresce at a second wavelength, different from said first wavelength.

PCT9. The process of any preceding paragraph, wherein said product is a cigarette rod which is wrapped in paper.

PCT10. The process of any preceding paragraph, wherein said product is a food product.

PCT11. The process of any preceding paragraph, wherein one or both of the fluorescent taggants is oil soluble.

PCT12. The process of any preceding paragraph, wherein one or both of the fluorescent taggants is oil dispersible.

PCT13. A process for detecting oil or lubricant contamination in a tobacco product, the process comprising: adding at least two fluorescent taggants to oils or lubricants contained in processing machinery for said product; irradiating said product, causing at least one of said taggants to fluoresce; and detecting radiation emitted by said fluorescing taggant in an oil-contaminated product.

PCT14. A process for identifying the source of oil contamination of products produced in a manufacturing process having multiple machines in series, each containing one or more oils or lubricants, comprising: adding a first fluorescent taggant to all of the oils or lubricants of each machine in the series; adding a second fluorescent taggant to each oil or lubricant of each machine in the series, different from said first fluorescent taggant and unique to each oil or lubricant of each machine in the series; irradiating the product with a first radiation spectrum and detecting radiation emitted by the first fluorescent taggant; and removing the radiation emitting product from the process.

PCT15. The process of paragraph PCT14, further comprising irradiating the removed product with a second radiation spectrum and detecting radiation emitted by said second fluorescent taggant, so as to identify the source of said contamination.

PCT16. The process of paragraph PCT15, wherein detection of radiation emitted by said second fluorescent taggant is conducted with an electronic radiation detection apparatus.

PCT17. The process of any of paragraphs PCT14-PCT16, wherein detection of radiation emitted by the first fluorescent taggant is conducted visually by an operator of said process.

PCT18. The process of any of paragraphs PCT14-PCT17, wherein the first fluorescent taggant is added to said oils or lubricants at a sufficient concentration level for its emission to be visually detectable by an operator of said process.

PCT19. The process of any of paragraphs PCT14-PCT18, wherein said fluorescent taggants are Stokes-shifting taggants, which absorb radiation at a first wavelength and fluoresce at a second wavelength, different from said first wavelength.

PCT20. The process of paragraph PCT19, wherein at least said first fluorescent taggant absorbs radiation in the ultraviolet spectrum and emits radiation in the visible spectrum.

INDUSTRIAL APPLICABILITY

The apparatus and methods disclosed herein are applicable to the consumer products industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

While the present invention has been described and illustrated by reference to particular forms, those of ordinary skill in the art will appreciate that the invention lends itself to variations not necessarily illustrated herein. For this reason, then, reference should be made solely to the appended claims for purposes of determining the true scope of the present invention.

We claim:

1. A process for detecting lubricant contamination in a manufactured product, the process comprising:
    adding a first fluorescent taggant and a second fluorescent taggant to a lubricant used in processing machinery for the product, the first fluorescent taggant being different than the second fluorescent taggant;
    irradiating the product with a first radiation spectrum, wherein the irradiation causes the first fluorescent taggant to fluoresce;
    visually detecting radiation emitted by the fluorescing first fluorescent taggant by an operator of the process;
    irradiating the product with a second radiation spectrum, wherein the irradiation causes the second fluorescent taggant to fluoresce; and
    electronically detecting radiation emitted by the fluorescing second fluorescent taggant by an electronic radiation detection device.

2. The process of claim 1, wherein the first fluorescent taggant, the second fluorescent taggant, or both the first fluorescent taggant and the second fluorescent taggant fluoresces upon irradiation with ultraviolet radiation.

3. The process of claim 2, wherein the first fluorescent taggant, the second fluorescent taggant, or both the first fluorescent taggant and the second fluorescent taggant emits radiation in the visible spectrum.

4. The process of claim 1, wherein both of the first fluorescent taggant and the second fluorescent taggant fluoresce upon irradiation with ultraviolet radiation.

5. The process of claim 1, wherein the first fluorescent taggant and the second fluorescent taggant are added to the lubricant at different concentration levels, with the first fluorescent taggant, the second fluorescent taggant, or both the first fluorescent taggant and the second fluorescent taggant being added at a sufficient concentration level for an emission to be visually detectable by the operator of the process.

6. The process of claim 1, wherein the first fluorescent taggant, the second fluorescent taggant, or both the first fluorescent taggant and the second fluorescent taggant is added to the lubricant at a concentration of about 50 ppb to about 100 ppm.

7. The process of claim 1, further comprising:
conveying the product past an electronic radiation detection apparatus that detects radiation emitted by the fluorescing second fluorescent taggant.

8. The process of claim 1, wherein the first fluorescent taggant and the second fluorescent taggant are Stokes-shifting taggants that absorb radiation at a first wavelength and fluoresce at a second wavelength, the second wavelength different from the first wavelength.

9. The process of claim 1, wherein the product is a cigarette rod wrapped in paper.

10. The process of claim 1, wherein the product is a food product.

11. The process of claim 1, wherein the first fluorescent taggant, the second fluorescent taggant, or both the first fluorescent taggant and the second fluorescent taggant are oil soluble.

12. The process of claim 1, wherein the first fluorescent taggant, the second fluorescent taggant, or both the first fluorescent taggant and the second fluorescent taggant are oil dispersible.

13. A process for detecting lubricant contamination in a tobacco product, the process comprising:
adding a first fluorescent taggant and a second fluorescent taggant to a lubricant used in processing machinery for the product, the first fluorescent taggant being different than the second fluorescent taggant;
irradiating the product with a first radiation spectrum, wherein the irradiation causes the first fluorescent taggant to fluoresce;
visually detecting radiation emitted by the fluorescing first fluorescent taggant by an operator of the process;
irradiating the product with a second radiation spectrum, wherein the irradiation causes the second fluorescent taggant to fluoresce; and
electronically detecting radiation emitted by the fluorescing second fluorescent taggant by an electronic radiation detection device.

14. The process of claim 13, wherein the first fluorescent taggant, the second fluorescent taggant, or both the first fluorescent taggant and the second fluorescent taggant fluoresce upon irradiation with ultraviolet radiation.

15. The process of claim 14, wherein the first fluorescent taggant, the second fluorescent taggant, or both the first fluorescent taggant and the second fluorescent taggant emit radiation in the visible spectrum.

16. The process of claim 13, wherein both of the first fluorescent taggant and the second fluorescent taggant fluoresce upon irradiation with ultraviolet radiation.

17. The process of claim 13, wherein the first fluorescent taggant and the second fluorescent taggant are added to the lubricant at different concentration levels, with the first fluorescent taggant, the second fluorescent taggant, or both the first fluorescent taggant and the second fluorescent taggant being added at a sufficient concentration level for its emission to be visually detectable by the operator of the process.

18. The process of claim 13, wherein the first fluorescent taggant, the second fluorescent taggant, or both the first fluorescent taggant and the second fluorescent taggant are added to the lubricant at a concentration of about 50 ppb to about 100 ppm.

19. The process of claim 13, further comprising:
conveying the product past an electronic radiation detection apparatus that detects radiation emitted by the fluorescing second fluorescent taggant.

20. The process of claim 13, wherein the first fluorescent taggant and the second fluorescent taggant are Stokes-shifting taggants that absorb radiation at a first wavelength and fluoresce at a second wavelength, the second wavelength different from the first wavelength.

21. The process of claim 13, wherein the product is a cigarette rod wrapped in paper.

22. The process of claim 13, wherein the first fluorescent taggant, the second fluorescent taggant, or both the first fluorescent taggant and the second fluorescent taggant are oil soluble.

23. The process of claim 13, wherein the first fluorescent taggant, the second fluorescent taggant, or both the first fluorescent taggant and the second fluorescent taggant are oil dispersible.

24. A process for identifying a source of oil contamination of a product produced in a manufacturing process having multiple machines in series, each of the multiple machines containing a lubricant, comprising:
adding a first fluorescent taggant to the lubricant of each machine in the series;
adding a second fluorescent taggant to the lubricant of each machine in the series, the second fluorescent taggant being different from the first fluorescent taggant, and the second fluorescent taggant of each machine in the series being different from the second fluorescent taggant in other machines in the series;
irradiating the product with a first radiation spectrum;
visually detecting radiation emitted by the first fluorescent taggant by an operator of the process;
removing the radiation emitting product from the process;
irradiating the radiation emitting product with a second radiation spectrum; and
electronically detecting radiation emitted by the second fluorescent taggant by an electronic radiation detection device.

25. The process of claim 24, further comprising:
identifying the source of the lubricant contamination based on the detected radiation emitted by the second fluorescent taggant.

26. The process of claim 24, wherein the first fluorescent taggant is added to the lubricant at a sufficient concentration level for its emission to be visually detectable by the operator of the process.

27. The process of claim 24, wherein the first fluorescent taggant and the second fluorescent taggant are Stokes-shifting taggants that absorb radiation at a first wavelength and fluoresce at a second wavelength, different from the first wavelength.

28. The process of claim 27, wherein the first fluorescent taggant or the first fluorescent taggant and the second fluorescent taggant absorbs radiation in the ultraviolet spectrum and emits radiation in the visible spectrum.

29. The process of claim 24, wherein at least one of the multiple machines is a machine for preparing a raw material for shipping.

30. The process of claim 24, wherein at least one of the multiple machines is a packaging machine.

31. The process of claim 24, wherein the electronic radiation detection device is mounted on or within at least one of the multiple machines in the series.

32. The process of claim 1, wherein the first fluorescent taggant is added to the lubricant at a concentration of about 50 ppb to about 100 ppm and the second fluorescent taggant is added to the lubricant at a concentration of less than about 50 ppb.

33. The process of claim 13, wherein the first fluorescent taggant is added to the lubricant at a concentration of about 50 ppb to about 100 ppm and the second fluorescent taggant is added to the lubricant at a concentration of less than about 50 ppb.

34. The process of claim 24, wherein the first fluorescent taggant is added to the lubricant at a concentration of about 50 ppb to about 100 ppm and the second fluorescent taggant is added to the lubricant at a concentration of less than about 50 ppb.

35. The process of claim 1, wherein the lubricant is oil.

36. The process of claim 13, wherein the lubricant is oil.

* * * * *